(12) United States Patent
Goode et al.

(10) Patent No.: US 7,950,155 B2
(45) Date of Patent: May 31, 2011

(54) SLITTING TOOL

(75) Inventors: Johnson E. Goode, Maple Grove, MN (US); Ron A. Drake, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 1192 days.

(21) Appl. No.: 11/343,349

(22) Filed: Jan. 31, 2006

(65) Prior Publication Data

US 2007/0175049 A1 Aug. 2, 2007

(51) Int. Cl.
| | |
|---|---|
| *B21F 13/00* | (2006.01) |
| *B26B 27/00* | (2006.01) |
| *B26B 3/00* | (2006.01) |
| *B26B 29/00* | (2006.01) |
| *A61B 17/08* | (2006.01) |
| *A61B 17/24* | (2006.01) |
| *A61F 11/00* | (2006.01) |
| *A61M 5/178* | (2006.01) |

(52) U.S. Cl. ............ 30/90.1; 30/90.4; 30/280; 30/289; 606/161; 606/153; 604/164.05

(58) Field of Classification Search .......... 606/161, 606/167, 158, 185, 153; 604/164.05, 523; 30/280, 294, 289, 2, 90.4; 83/614
See application file for complete search history.

(56) References Cited

U.S. PATENT DOCUMENTS

| | | | |
|---|---|---|---|
| 2,018,149 A * | 10/1935 | Randle et al. ............ 30/2 |
| 3,057,232 A | 10/1962 | Cornell | |
| 3,624,901 A | 12/1971 | Pettit et al. | |
| 3,793,682 A | 2/1974 | Nelson | |
| 3,898,733 A * | 8/1975 | Cormier ................ 30/90.4 |
| 4,394,828 A | 7/1983 | Garbis et al. | |
| 4,631,059 A | 12/1986 | Wolvek et al. | |
| 4,687,469 A | 8/1987 | Osypka | |
| 4,997,424 A * | 3/1991 | Little ................ 604/161 |

(Continued)

FOREIGN PATENT DOCUMENTS

WO WO 01/02047 A1 1/2001

(Continued)

OTHER PUBLICATIONS

Medtronic Technical Manual for the 6218RED Guide Catheter Slitter.

(Continued)

*Primary Examiner* — Ghassem Alie
*Assistant Examiner* — Bharat C Patel
(74) *Attorney, Agent, or Firm* — Mueting, Raasch & Gebhardt, P.A.

(57) ABSTRACT

A tool for slitting an elongate sheath from about an elongate member that is disposed within a longitudinally extending lumen of the sheath includes a longitudinally extending tail portion projecting rearward of a slitting edge and a nose portion of the tool; a lower surface of the nose portion is disposed beneath the slitting edge for engaging a portion of the elongate member. The tail portion of the tool, approximately aligned with the sheath lumen when the lower surface engages the elongate member and a leading edge of the nose portion is within the sheath lumen, is sized to fit within the sheath lumen after the sheath is slit by the slitting edge. A passageway between the nose portion and the tail portion allows a proximal segment of the elongate member to bend away from the tail portion when the elongate member is engaged by the nose portion.

14 Claims, 6 Drawing Sheets

U.S. PATENT DOCUMENTS

| | | | |
|---|---|---|---|
| 5,188,606 A | | 2/1993 | Maloney et al. |
| 5,261,887 A | * | 11/1993 | Walker .................... 604/161 |
| 5,330,460 A | * | 7/1994 | Moss et al. ................ 30/90.4 |
| 5,359,690 A | | 10/1994 | Kaizu et al. |
| 5,687,727 A | | 11/1997 | Kraus et al. |
| 5,873,858 A | | 2/1999 | Schafer et al. |
| D433,929 S | | 11/2000 | Petzl |
| 6,148,521 A | * | 11/2000 | Eslambolchi et al. ........ 30/90.4 |
| 6,159,198 A | | 12/2000 | Gardeski et al. |
| 6,247,235 B1 | | 6/2001 | Lawler |
| 6,334,253 B1 | | 1/2002 | Cheng |
| 6,368,337 B1 | | 4/2002 | Kieturakis et al. |
| 6,497,681 B1 | * | 12/2002 | Brenner ................. 604/164.05 |
| 6,544,247 B1 | * | 4/2003 | Gardeski et al. ............. 604/510 |
| 7,029,460 B2 | | 4/2006 | Gardeski et al. |
| 7,338,481 B2 | | 3/2008 | Gardeski et al. |
| D576,279 S | | 9/2008 | Bullemer et al. |
| D576,280 S | | 9/2008 | Bullemer et al. |
| 7,462,167 B2 | | 12/2008 | Kratz et al. |
| 2003/0158565 A1 | | 8/2003 | Gardeski et al. |
| 2003/0181935 A1 | | 9/2003 | Gardeski et al. |
| 2005/0182435 A1 | * | 8/2005 | Andrews et al. ............. 606/172 |
| 2007/0079511 A1 | * | 4/2007 | Osypka ..................... 30/90.1 |
| 2009/0049698 A1 | | 2/2009 | Drake et al. |
| 2009/0054840 A1 | | 2/2009 | Drake et al. |
| 2009/0071012 A1 | | 3/2009 | Shan et al. |
| 2010/0030154 A1 | | 2/2010 | Duffy |
| 2011/0000089 A1 | | 1/2011 | Goode et al. |

FOREIGN PATENT DOCUMENTS

| | | |
|---|---|---|
| WO | WO 2006/085119 A1 | 8/2006 |
| WO | WO 2007/089985 A1 | 8/2007 |
| WO | WO 2009/029558 A2 | 3/2009 |
| WO | WO 2009/029573 A1 | 3/2009 |
| WO | WO 2009/029558 A3 | 9/2009 |
| WO | WO 2010/014419 A1 | 2/2010 |

OTHER PUBLICATIONS

U.S. Appl. No. 29/323,518, filed Aug. 27, 2008, Bullemer et al.
U.S. Appl. No. 29/323,574, filed Aug. 27, 2008, Bullemer et al.
International Search Report for PCT application No. PCT/US2007/060664, May 4, 2007; 2 pgs.
International Preliminary Report on Patentability and Written Opinion for PCT application No. PCT/US2007/060664, Aug. 5, 2008; 6 pgs.

* cited by examiner

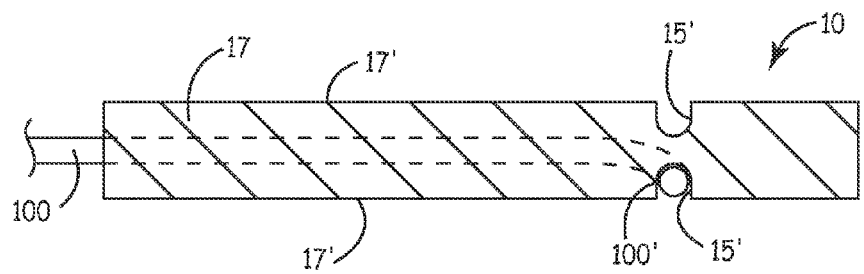
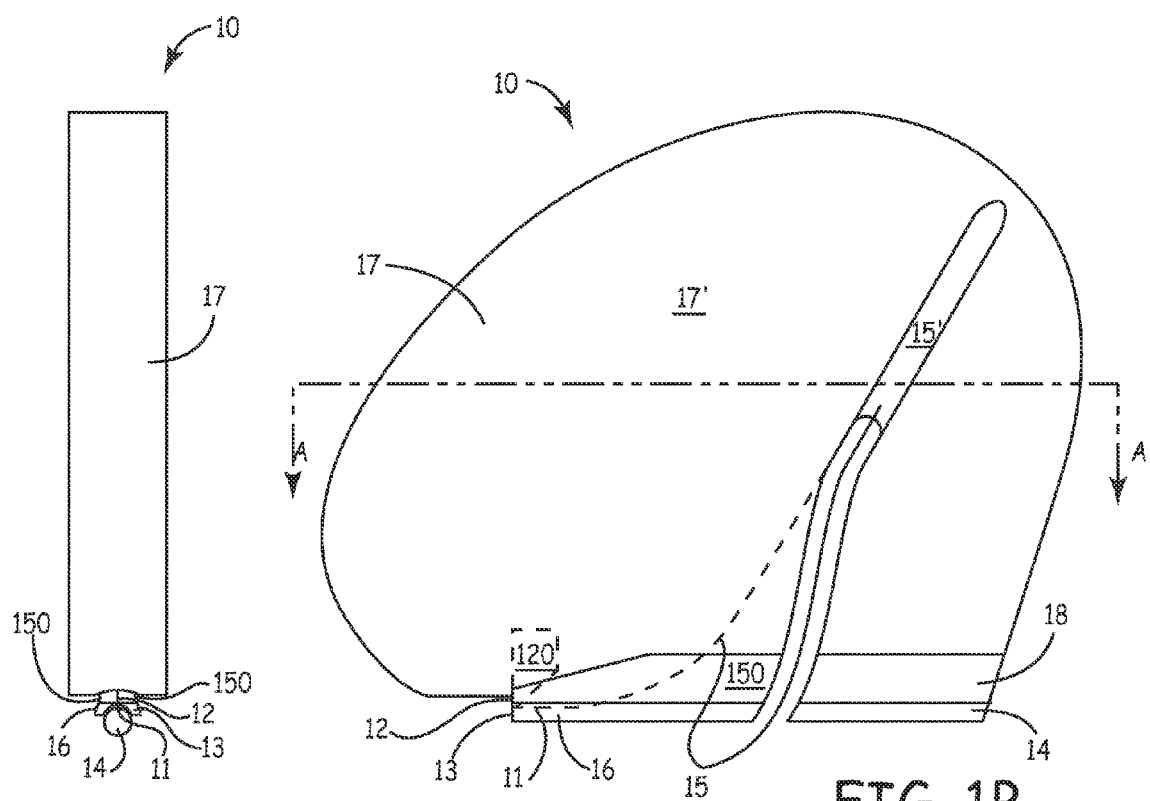

SLITTING TOOL

FIELD OF THE INVENTION

The present invention pertains to slitting tools and more particularly to slitting tools facilitating removal of an elongate sheath or catheter from about an elongate member disposed therein.

BACKGROUND OF THE INVENTION

Sheaths, or catheters, are commonly used in minimally invasive medical procedures, for example, to provide a pathway for the introduction of elongate medical devices into the vascular system of a patient. Many medical devices, introduced in such a manner, through a lumen of the sheath, are intended to indwell within the patient for a prolonged period, for example, extending from a number of days to many years. After the indwelling medical device has been inserted within the lumen of the sheath, for positioning within the patient, it is desirable to remove the sheath from the patient without dislodging the indwelling device.

A number of slitting tools, known to those skilled in the art, are used to remove sheaths from about indwelling medical devices. However, these tools present one or more difficulties to the user, for example, with respect to handling.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIGS. 1A-B are an end view and a side plan view, respectively, of a slitting tool according to one embodiment of the present invention.

FIG. 1C is a section view through section line A-A of FIG. 1B.

DETAILED DESCRIPTION OF THE ILLUSTRATED EMBODIMENTS

Figure 2:
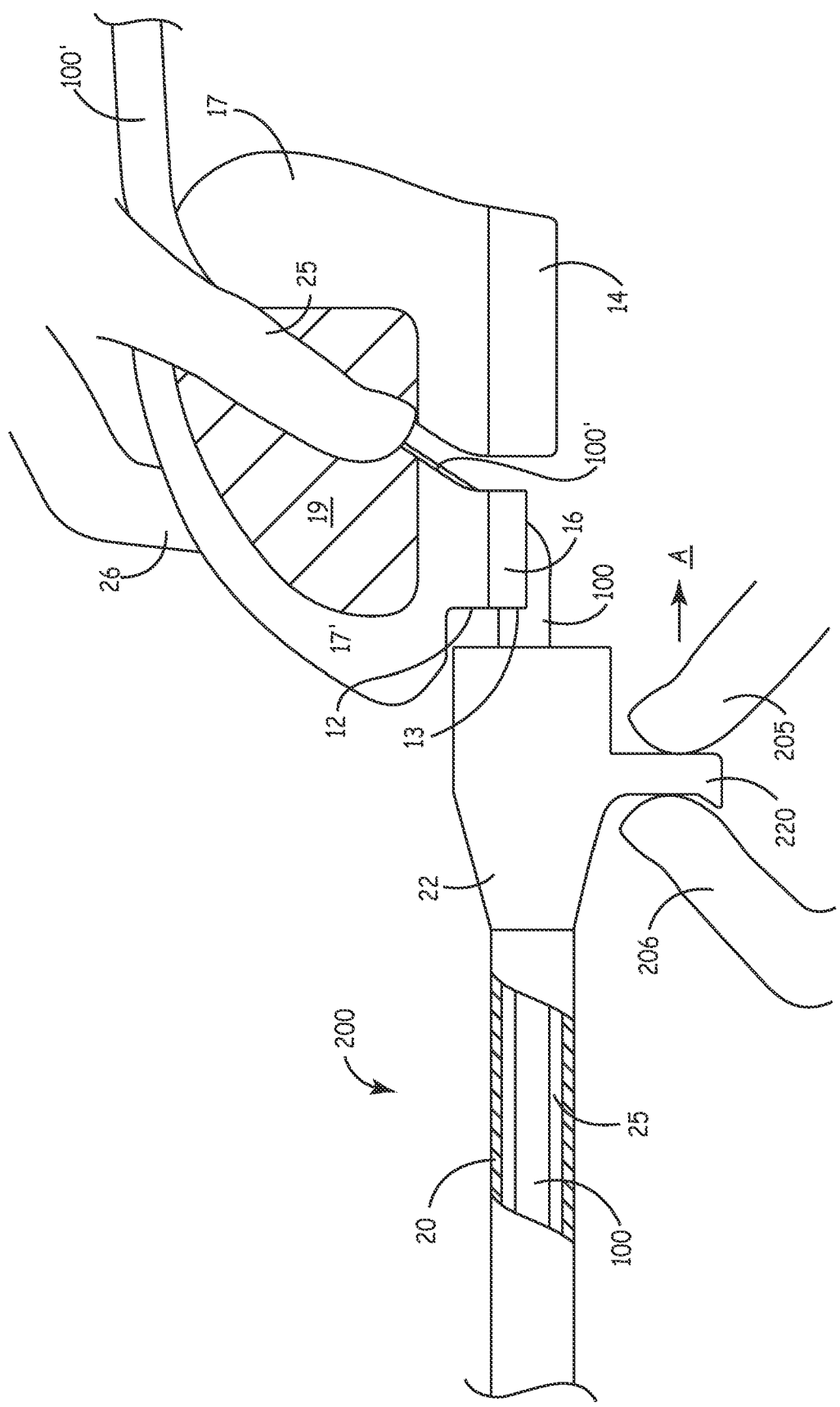
FIG. 2 is a schematic plan view, including a partial section, depicting a method for using a slitting tool according to some embodiments of the present invention.

The following detailed description is exemplary in nature and is not intended to limit the scope, applicability, or configuration of the invention in any way. Rather, the following description provides practical illustrations for implementing exemplary embodiments of the present invention.

FIGS. 1A-B are an end view and a side plan view, respectively, of a slitting tool 10, according to one embodiment of the present invention; and FIG. 1C is a section view through line A-A of FIG. 1B. FIGS. 1A-C illustrate tool 10 including a nose portion 16, a handle portion 17, a slitting edge 12 extending between nose portion 16 and handle portion 17, a longitudinally extending tail portion 14, and a passageway 15 disposed between nose portion 16 and tail portion 14, and extending upward into handle portion 17. FIGS. 1A-B further illustrate nose portion 16 including a lower surface 11 and a leading edge 13. According to the illustrated embodiment, slitting edge 12 is part of a metallic blade member 120 mounted in handle 17; according to alternate embodiments, slitting edge is an integral part of material forming tool 10 as a whole. Tool 10 may be formed of a rigid plastic, a ceramic, a metallic material or a combination thereof.

According to the illustrated embodiment, lower surface 11 of nose portion 16 is adapted to engage an elongate member 100, and FIG. 1C shows elongate member 100 extending from nose portion 16 into passageway 15 such that a proximal segment 100' of member 100 bends away from tail portion 14. With reference to FIGS. 1B-C, passageway 15 extends from nose portion 16 up into handle 17, being flanked on either side by a sidewall 150; passageway 15 further extends into grooves 15', which are formed along opposing outer surfaces 17' of handle 17 and either of which can accommodate segment 100'. An operator, gripping handle 17 of tool 10, may hold proximal segment 100' of elongate member 100 in one of channel grooves 15', as illustrated in FIG. 2.

FIG. 2 is a schematic plan view, including a partial section, depicting a method for using slitting tool 10 according to some embodiments of the present invention. FIG. 2 illustrates elongate member 100, for example, an implantable medical electrical lead, disposed within a lumen 25 of a sheath 200; sheath 200 is shown including a tubular sheath wall 20 terminated at a proximal end by a hub 22. FIG. 2 further illustrates a first thumb 25 and forefinger 26 of an operator holding slitting tool 10 and proximal segment 100' of member 100, while a second thumb 205 and forefinger 206 hold a hub handle 220 to pull sheath 200, per arrow A, against slitting edge 12 of tool 10. Nose portion 16 of tool 10 is shown engaging elongate member 100 while proximal segment 100' bends through passageway 15 that extends along an operator grip zone 19, which, on opposing surfaces 17' of handle 17, is generally located in the zone indicated by cross-hatching. According to the illustrated embodiment, tail portion 14 of tool 10 is approximately aligned with sheath lumen 25 and is sized to fit within sheath lumen 25, when slit, so that tail portion 14 will ride within sheath lumen 25 after slitting edge 12 cuts through hub and sheath wall 20. According to some embodiments, tail portion 14 further includes a profile closely conforming with slit sheath lumen 25, for example as illustrated in FIG. 3B.

Figure 3A:
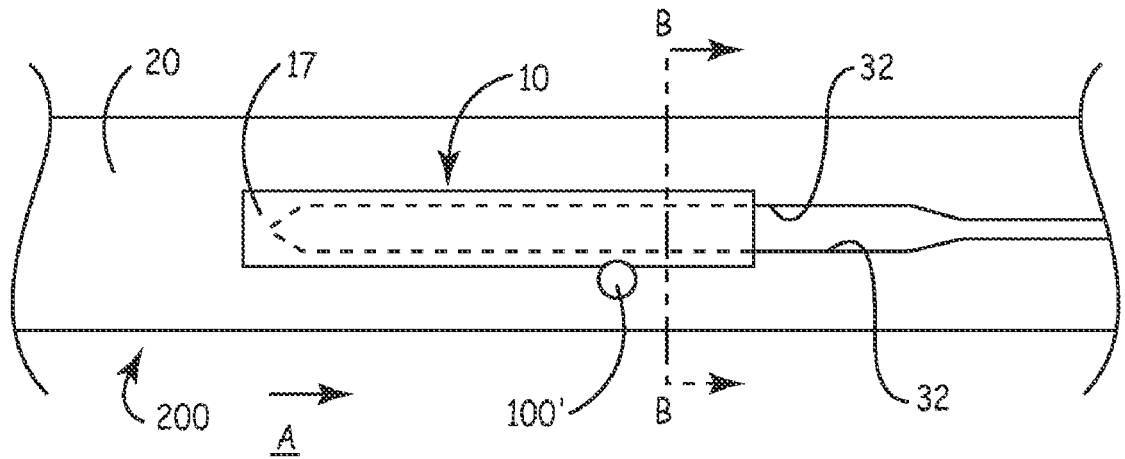
FIG. 3A is a top view of the slitting tool, shown in FIGS. 1A-C, cutting through a portion of a sheath wall.
Figure 3B:
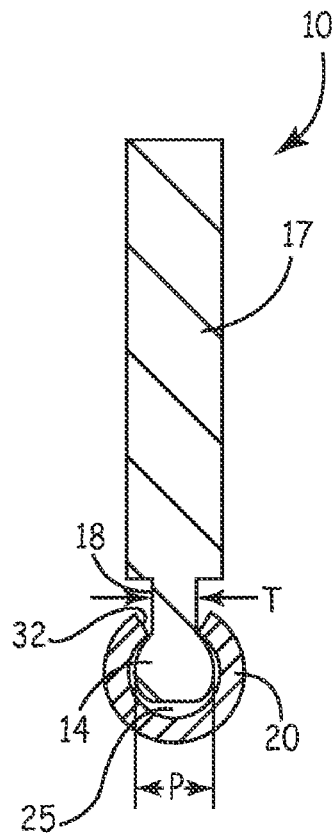
FIG. 3B is a section view through section line B-B of FIG. 3A.

FIG. 3A is a top view of the slitting tool, shown in FIGS. 1A-C, cutting through a portion of sheath wall 20; and FIG. 3B is a section view through section line B-B of FIG. 3A. FIGS. 3A-B illustrate sheath 200 having been pulled, per arrow A, so that sheath wall 20 has been slit by tool slitting edge 12 (FIGS. 1A-B and 2) and tool tail portion 14 is disposed within lumen 25, downstream of slitting edge 12; slit edges 32 of sheath wall 20 emanate from slitting edge 12 beneath tool handle 17, shown by dashed lines, and extend downstream of tool 10; fingers 25, 26 and associated hand of the operator holding tool 10 (FIG. 2) are not shown so that the view of tool 10 and slit edges 32 of sheath wall 20 is not obstructed. FIG. 3B further illustrates a profile of tail portion 14, formed by a continuous exterior surface extending thereabout, which closely mates with slit sheath lumen 25; a width P of tail portion 14 may be approximately equal to or slightly greater than a pre-slit diameter of sheath lumen 25, or may be up to two times greater than the pre-slit diameter of lumen 25. FIG. 3B further illustrates tool 10 including a shank 18 joining handle 17 to tail portion 14; according to some embodiments, a thickness T of shank 18 is greater than approximately 0.01 inch and less than width P of tail portion 14.

According to embodiments of the present invention, tail portion 14 may serve to stabilize tool 10 as it cuts through sheath wall 20 and may further prevent slit edges 32 from collapsing toward one another in a way which may cause slit sheath lumen 25 to 'grab' elongate member 100, as sheath 200 is pulled, per arrow A, thereby dislodging a distal end of member 100. An effective length of tail portion 14, for stabilizing tool 10 as it cuts through sheath wall 20, may be approximately equal to or greater than ½ inch. Although, in FIG. 2, tail portion 14 is illustrated extending proximally from operator grip zone 19 of handle portion 17, embodiments of the present invention are not so limited.

Figure 4A:
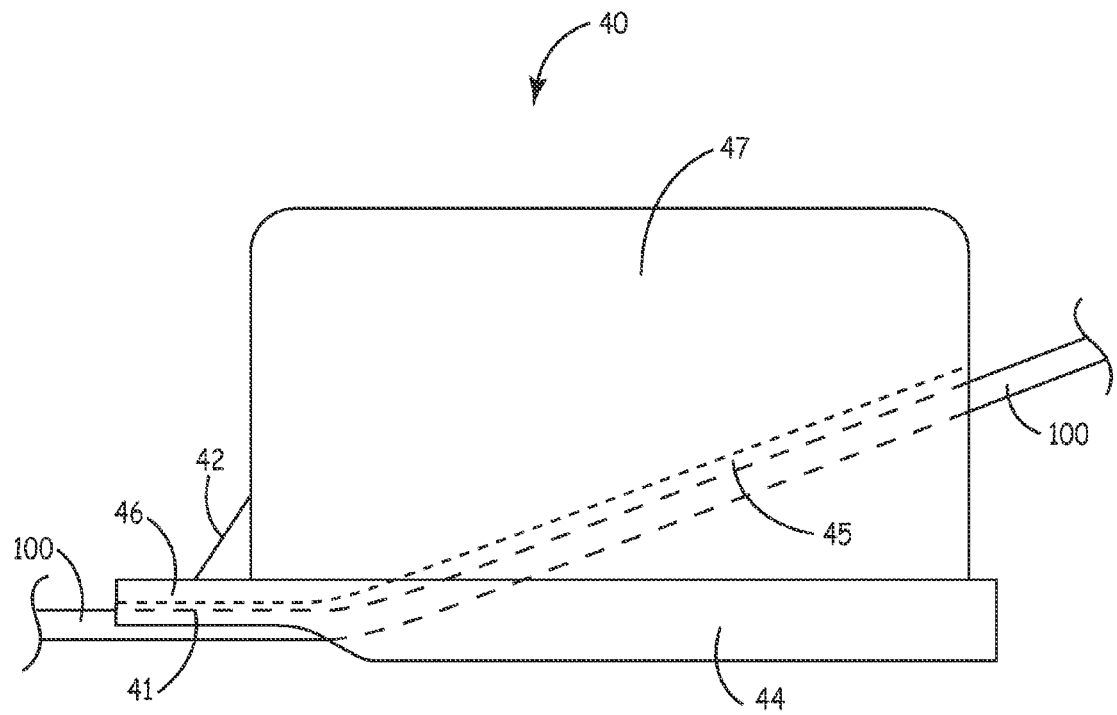
FIGS. 4A-B are a side plan view and an end view of a slitting tool according to another embodiment of the present invention.
Figure 4B:
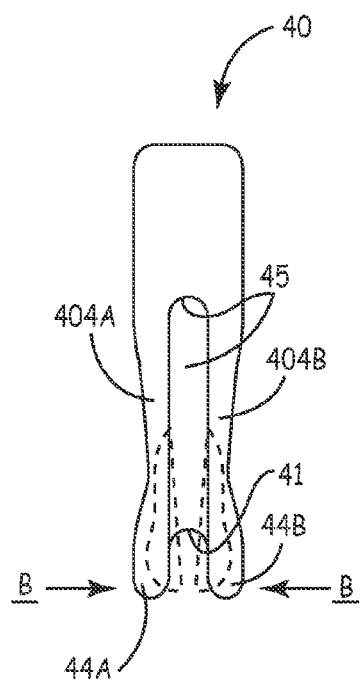

FIGS. 4A-B are a side plan view and an end view of a slitting tool 40 according to another embodiment of the present invention. FIGS. 4A-B illustrate tool 40 including a nose portion 46, a handle portion 47, a slitting edge 42 extending between nose portion 46 and handle portion 47, and a longitudinally extending tail portion 44. FIGS. 4A-B further illustrate nose portion 46 including a lower surface 41 extending from a leading edge 43 to a passageway 45 that extends from between nose portion 46 and tail portion 44, upward into handle portion 47. According to the illustrated embodiment, to facilitate loading of elongate member 100 into passageway 45, for example, as shown in FIG. 4A, tail portion 44 is split into a first leg 404A and a second leg 404B. FIG. 4B shows each leg 404A, B including a foot 44A and 44B, respectively; feet 44A, B together form a tail profile, to mate with a slit lumen of a sheath or catheter, when legs are forced, per arrows B, together, as shown with dashed lines; the resulting profile is similar to that of solid tail 14 illustrated in FIG. 3B. Legs 404A, B would be forced together in such a way when a sheath is pulled past slitting edge 42 of tool 40 such that tail 44 is enclosed by the slit lumen of the sheath.

Figure 5A:
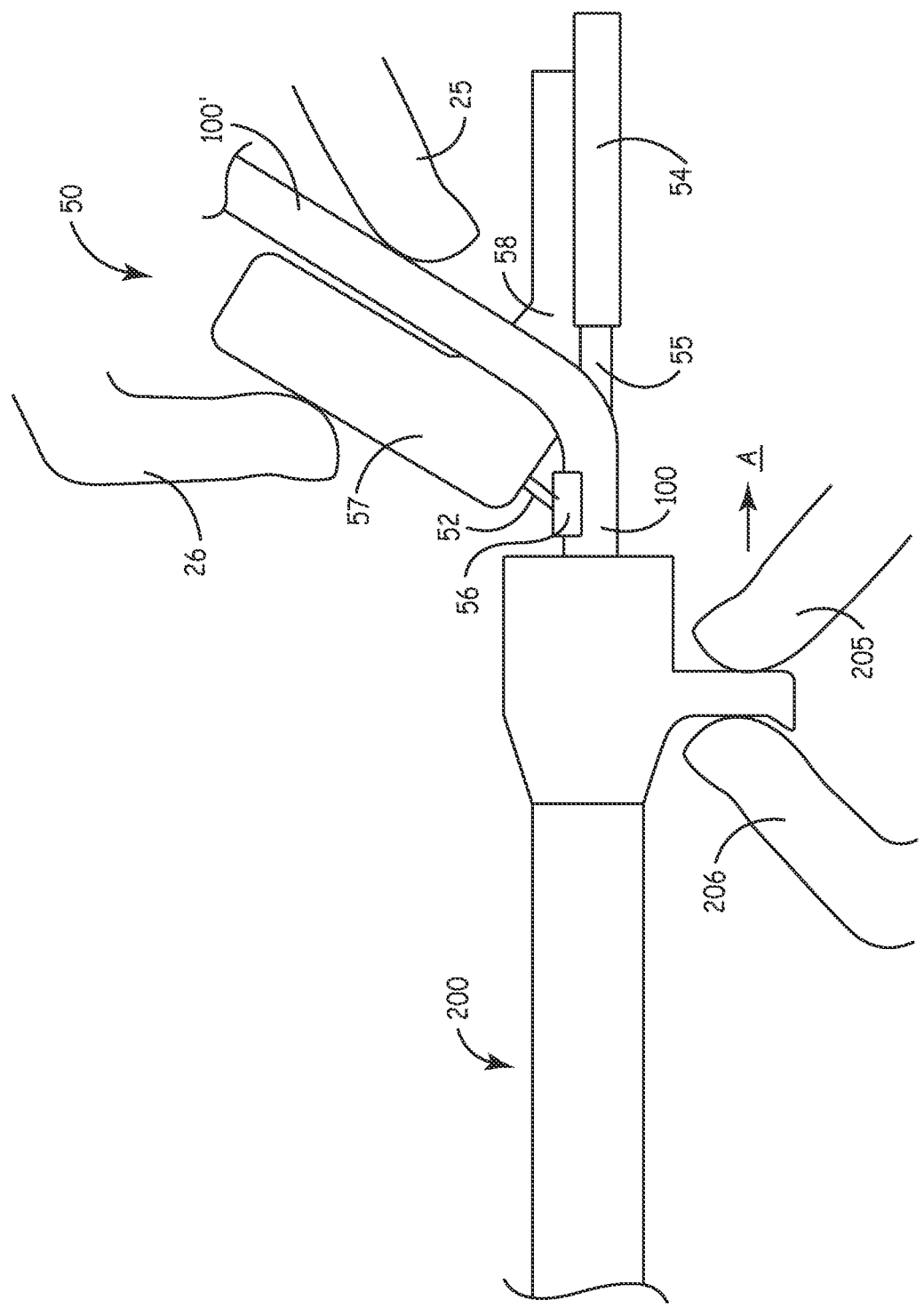
FIG. 5A is a schematic showing an alternate embodiment of a slitting tool in a position for slitting a sheath.
Figure 5B:
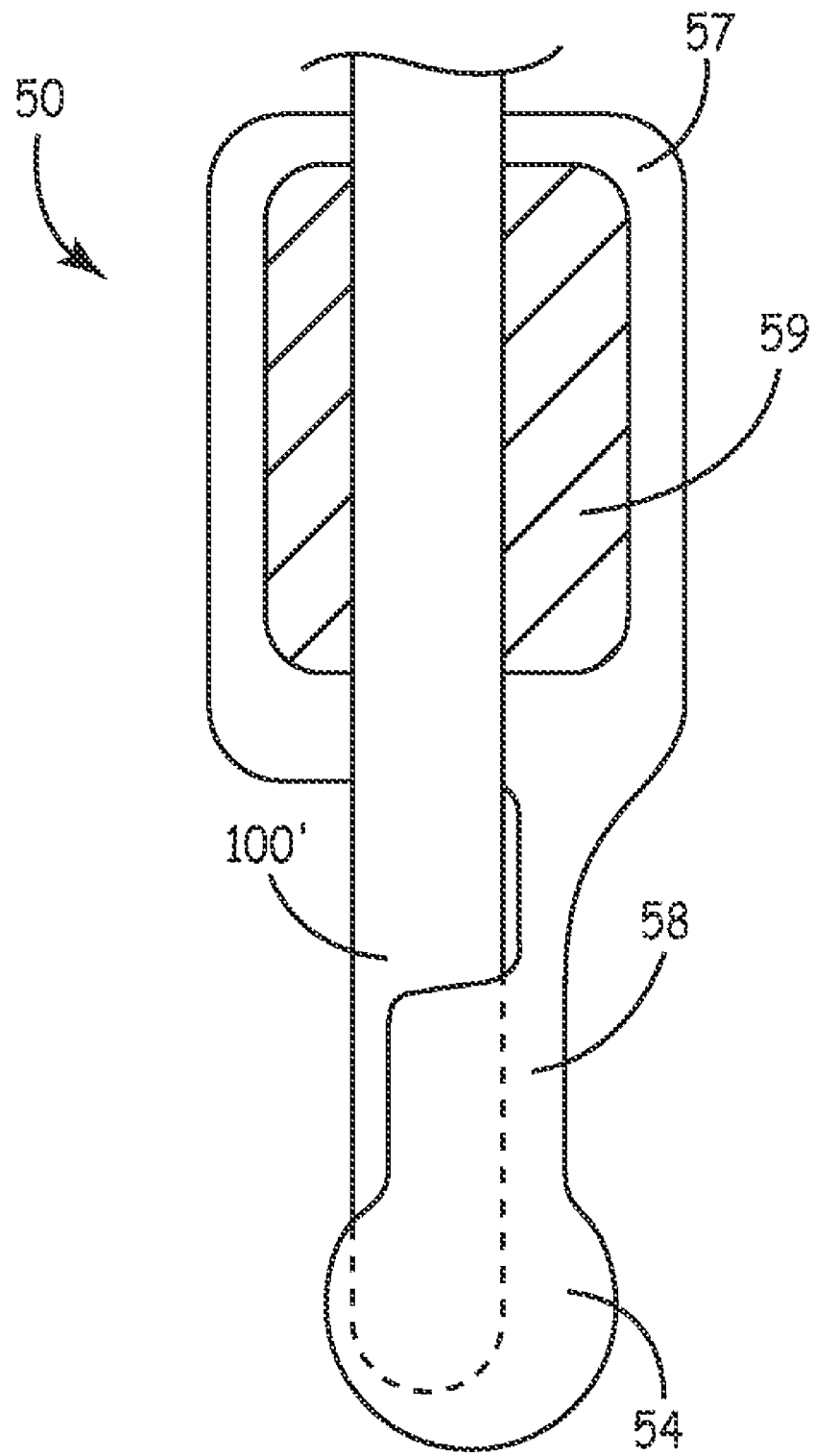
FIG. 5B is an end view of FIG. 5A.

FIG. 5A is a schematic showing an alternate embodiment of a slitting tool 50 in a position for slitting sheath 200; and FIG. 5B is an end view of FIG. 5A. FIG. 5A illustrates tool 50 including a nose portion 56, a handle portion 57, a slitting edge 52, extending between nose portion 56 and handle portion 57, and a longitudinally extending tail portion 54, which is joined to handle portion 57 by a shank 58. FIG. 5A further illustrates nose portion 56 engaging elongate member 100 and a passageway 55, disposed between nose portion 56 and tail portion 54, allowing proximal segment 100' of elongate member 100 to bend away from tail portion 54. According to the illustrated embodiment, fingers 25 and 26, associated with the hand of the operator, hold segment 100' against an operator grip zone 59 of handle 57, the extent of which generally corresponds to the cross-hatched area shown in FIG. 5B.

In the foregoing detailed description, the invention has been described with reference to specific embodiments. However, it may be appreciated that various modifications and changes can be made without departing from the scope of the invention as set forth in the appended claims.

The invention claimed is:

1. A tool for slitting an elongate sheath from about an elongate member disposed within a longitudinally extending lumen of the elongate sheath, the tool comprising:
   a slitting edge;
   a nose portion disposed beneath the slitting edge, the nose portion including a lower surface open downward for engaging a portion of the elongate member, the nose portion comprising a rear portion and a leading edge;
   a handle portion projecting upward from the nose portion and rearward of the slitting edge;
   a longitudinally extending tail portion projecting rearward of the slitting edge and rear portion of the nose portion, the tail portion extending between a first end and a second end along a longitudinal axis downwardly from a portion of the handle and approximately aligned with the sheath lumen when the lower surface of the nose portion engages the elongate member and the leading edge of the nose portion is within the sheath lumen, the tail portion including a profile closely conforming with the sheath lumen after the sheath is slit by the slitting edge such that the tail portion mates within the slit sheath lumen and prevents the slit edges of the sheath from collapsing toward one another, wherein the tail portion comprises one or more exterior surfaces foaming the profile closely conforming with the sheath lumen to mate within the slit sheath lumen, wherein the one or more exterior surfaces comprise at least opposing first and second curved exterior side surfaces, and further wherein the tail portion comprises a width about equal to or greater than a pre-slit diameter of the sheath lumen such that at least a portion of both the first curved exterior side surface and the second curved exterior side surface contact the sheath and mate within the slit sheath lumen; and
   a passageway disposed between the nose portion and the first end of the tail portion, wherein the passageway extends upward at the rear portion of the nose portion into the handle portion above and away from the tail portion, the passageway allowing a segment of the elongate member to bend away from the tail portion when the lower surface of the nose portion engages the portion of the elongate member and allowing at least a portion of the elongate member to be held in the passageway against the handle by one or more fingers of a user, the segment being proximal to the portion engaged by the lower surface.

2. The tool of claim 1, further comprising a shank extending upward from the tail portion, the shank including a thickness being greater than approximately 0.01 inch and less than approximately a maximum width of the profile of the tail portion.

3. The tool of claim 1, wherein the profile of the tail portion includes a maximum width being between approximately equal to a pre-slit diameter of the lumen and approximately two times greater than the pre-slit diameter of the sheath lumen.

4. The tool of claim 1, wherein the handle portion includes an operator grip zone and the tail portion further projects rearward of the grip zone.

5. The tool of claim 1, wherein the tail portion includes a longitudinal length greater than or equal to approximately one inch.

6. The tool of claim 1, wherein the first curved exterior side surface and the second curved exterior side surface of the tail portion form a portion of a continuous exterior surface extending around the profile mating with the slit sheath lumen.

7. The tool of claim 1, wherein the tail portion is split, including opposing interior surfaces.

8. A tool for slitting an elongate sheath from about an elongate member disposed within a longitudinally extending lumen of the elongate sheath, the tool comprising:
   a slitting edge;
   a nose portion disposed beneath the slitting edge, the nose portion including a lower surface open downward for engaging a portion of the elongate member, the nose portion comprising a rear portion and a leading edge;

a handle portion projecting upward from the lower surface of the nose portion and rearward of the slitting edge;

a longitudinally extending tail portion projecting rearward of the slitting edge and rear portion of the nose portion, the tail portion extending between a first end and a second end along a longitudinal axis downwardly from a portion of the handle and approximately aligned with the sheath lumen when the lower surface of the nose portion engages the elongate member and the leading edge of the nose portion is within the sheath lumen, the tail portion sized to fit within the sheath lumen after the sheath is slit by the slitting edge such that the tail portion mates within the slit sheath lumen and prevents the slit edges of the sheath from collapsing toward one another, wherein the tail portion comprises one or more exterior surfaces forming the tail portion sized to mate within the slit sheath lumen, wherein the one or more exterior surfaces comprise at least opposing first and second curved exterior side surfaces, and further wherein the tail portion comprises a width about equal to or greater than a pre-slit diameter of the sheath lumen such that at least a portion of both the first curved exterior side surface and the second curved exterior side surface contact the sheath and mate within the slit sheath lumen; and a passageway disposed between the nose portion and the first end of the tail portion, wherein the passageway extends upward at the rear portion of the nose portion into the handle portion above and away from the tail portion, the passageway allowing a segment of the elongate member to bend away from the tail portion when the lower surface of the nose portion engages the portion of the elongate member and allowing at least a portion of the elongate member to be held in the passageway against the handle using one or more fingers of a user, the segment being proximal to the portion engaged by the lower surface, and the tail portion projecting a distance greater than about ½ inch rearward of the passageway.

9. The tool of claim 8, further comprising a shank extending upward from the tail portion, the shank including a thickness being greater than approximately 0.01 inch and less than approximately a maximum width of a profile of the tail portion.

10. The tool of claim 8, wherein a profile of the tail portion includes a maximum width being between approximately equal to a pre-slit diameter of the lumen and approximately two times greater than the pre-slit diameter of the sheath lumen.

11. The tool of claim 8, wherein the first curved exterior side surface and the second curved exterior side surface of the tail portion a portion of a continuous exterior surface extending around a profile thereof sized to fit within the slit sheath lumen.

12. The tool of claim 8, wherein the tail portion is split, including opposing interior surfaces.

13. A tool for slitting an elongate sheath from about an elongate member disposed within a longitudinally extending lumen of the elongate sheath, the tool comprising:

a slitting edge;

a nose portion disposed beneath the slitting edge, the nose portion including a lower surface open downward for engaging a portion of the elongate member, the nose portion comprising a rear portion and a leading edge;

a longitudinally extending tail portion projecting rearward of the slitting edge and the rear portion of the nose portion, the tail portion extending between a first end and a second end along a longitudinal axis downwardly from a portion of the handle and approximately aligned with the sheath lumen when the lower surface of the nose portion engages the elongate member and the leading edge of the lower surface is within the sheath lumen, the tail portion sized to fit within the sheath lumen after the sheath is slit by the slitting edge and a continuous exterior surface extending around a profile thereof such that the tail portion mates within the slit sheath lumen and prevents the slit edges of the sheath from collapsing toward one another, wherein the continuous exterior surface extending around the profile comprises at least opposing first and second curved exterior side surfaces, and further wherein the tail portion comprises a width about equal to or greater than a pre-slit diameter of the sheath lumen such that at least a portion of both the first curved exterior side surface and the second curved exterior side surface contact the sheath and mate within the slit sheath lumen; and a passageway disposed between the nose portion and the first end of the tail portion, wherein the passageway extends upward at the rear portion of the nose portion into the handle above and away from the tail portion, the passageway allowing a segment of the elongate member to bend away from the tail portion when the lower surface of the nose portion engages the portion of the elongate member and allowing at least a portion of the elongate member to be held in the passageway against the handle by one or more fingers of a user, the segment being proximal to the portion engaged by the lower surface.

14. The tool of claim 13, further comprising a shank extending upward from the tail portion, the shank including a thickness being greater than approximately 0.01 inch and less than approximately a maximum width of a profile of the tail portion.

* * * * *